United States Patent
Leger et al.

(10) Patent No.: US 10,191,268 B2
(45) Date of Patent: Jan. 29, 2019

(54) METHOD FOR ANALYZING A SAMPLE WITH A NON-LINEAR MICROSCOPY TECHNIQUE AND NON-LINEAR MICROSCOPE ASSOCIATED

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR); ECOLE NORMALE SUPERIEURE, Paric (FR)

(72) Inventors: Jean-Francois Leger, Sceaux (FR); Laurnet Bourdieu, Pairs (FR); Stephane Dieudonne, Chatenay Malabry (FR)

(73) Assignees: INSERM (Institute National de la Sante et de la Recherche Medicale), Paris (FR); Centre National de la Recherche Scientifique (CNRS), Paris (FR); Ecole Normale Superieure, Paris (FR)

( * ) Notice: Subject to any disclaimer, the term of this patent is extended or adjusted under 35 U.S.C. 154(b) by 0 days.

(21) Appl. No.: 15/518,049

(22) PCT Filed: Oct. 15, 2015

(86) PCT No.: PCT/EP2015/073884
§ 371 (c)(1),
(2) Date: Apr. 10, 2017

(87) PCT Pub. No.: WO2016/059158
PCT Pub. Date: Apr. 21, 2016

(65) Prior Publication Data
US 2017/0242232 A1   Aug. 24, 2017

(30) Foreign Application Priority Data

Oct. 15, 2014 (EP) .................................. 14306634

(51) Int. Cl.
*G02F 1/33*    (2006.01)
*G02B 21/16*   (2006.01)
(Continued)

(52) U.S. Cl.
CPC ......... *G02B 21/16* (2013.01); *G01N 21/6458* (2013.01); *G02B 21/0036* (2013.01);
(Continued)

(58) Field of Classification Search
CPC ........ G02F 1/33; G02F 2201/16; G02F 1/113; G02F 1/29; G02F 2203/12; G02B 21/365;
(Continued)

(56) References Cited

U.S. PATENT DOCUMENTS

2006/0071143 A1*  4/2006  Saggau ................ G02B 21/002
250/201.3

* cited by examiner

Primary Examiner — Brandi Thomas
(74) Attorney, Agent, or Firm — W & C IP

(57) ABSTRACT

The present invention concerns a method for generating a pattern of light, this method comprising the following steps: a) emitting an input laser pulse (P1), b) deflecting the input laser pulse (P1) by a first deflector (22) to obtain a first laser pulse, c) deflecting the first laser pulse (P3) by a second deflector (24) to obtain a second laser pulse (P4), and d) focusing the pulse (P4) by an optical element characterized in that: —the first deflector (22) shapes the first laser pulse (P3) according to a first function, —the second deflector (24) shapes the second laser pulse (P4) according to a second function, and—the first function f(x) and the second function g(y) are computed and/or optimized to obtain the desired pattern of light.

15 Claims, 2 Drawing Sheets

(51) Int. Cl.
*G02B 21/00* (2006.01)
*G02B 26/10* (2006.01)
*G01N 21/64* (2006.01)
*G02F 1/11* (2006.01)
*G03H 1/00* (2006.01)

(52) U.S. Cl.
CPC ....... *G02B 21/0076* (2013.01); *G02B 26/101* (2013.01); *G02B 26/106* (2013.01); *G02F 1/113* (2013.01); *G02F 1/33* (2013.01); *G03H 1/0005* (2013.01); *G02B 2207/114* (2013.01); *G03H 2001/005* (2013.01)

(58) Field of Classification Search
CPC ................ G02B 21/002; G02B 21/006; G02B 26/0808; G02B 27/30; G02B 21/0036; G02B 21/0076; G02B 2207/114; G02B 21/06; G02B 21/16; G02B 26/101; G02B 26/106
USPC ............... 359/237, 238, 285, 286, 287, 289, 359/290–292, 298, 300, 305, 310
See application file for complete search history.

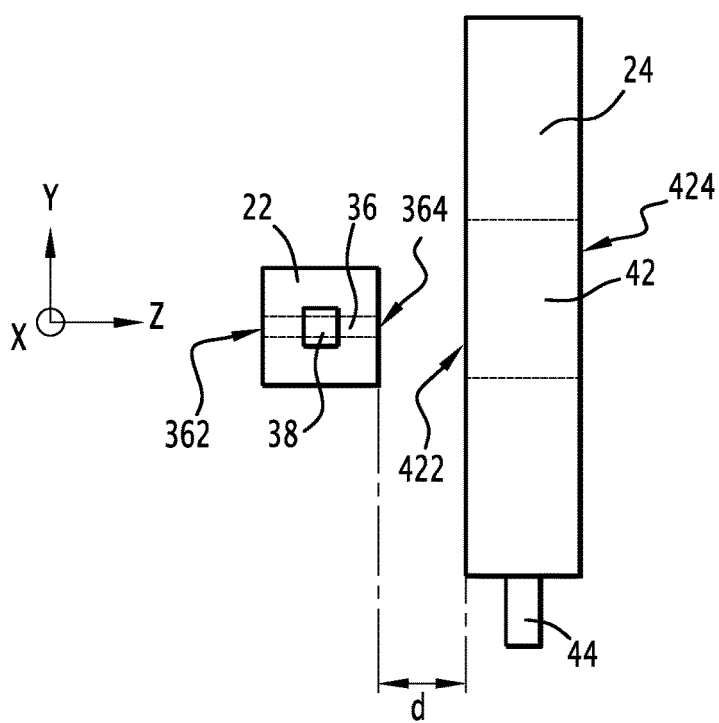

METHOD FOR ANALYZING A SAMPLE WITH A NON-LINEAR MICROSCOPY TECHNIQUE AND NON-LINEAR MICROSCOPE ASSOCIATED

TECHNICAL FIELD OF THE INVENTION

The invention relates to a method for analyzing or modifying a sample with a non-linear microscopy technique. The invention also concerns the non-linear microscope associated.

BACKGROUND OF THE INVENTION

In optical microscopy, the generation of patterns of light at high spatial and temporal resolution is desirable. In the present application, a pattern of light refers to the focusing of light at one or more spots at given positions in 2D and 3D and to the sculpting of the light intensity distribution in an extended pattern around these spots.

A pattern of light can be used to image the structure and activity of biological samples, such as neuronal dendrites. A pattern of light also enables to modify optically the biological activity or chemical environment of these biological samples. It is therefore desirable to be able to generate arbitrary light patterns at a high speed.

For this, it is known to carry out a three-dimensional scanning of a sample by using galvanometers for in-plane scanning and various mechanical designs for scanning along the optical axis (generally named Z-scanning). Such designs include displacement of optical elements such as lenses, displacement of optically-conjugated mirrors, or deformation of liquid lenses.

However, due to the poor spatio-temporal patterning capacity of both galvanometers and mechanical Z-scanning devices, the versatility of this approach is limited. It results in spatially constrained light pattern formation at a relatively low speed.

Spatially extended light patterns are produced by devices able to spatially shape the light in phase and/or amplitude, including mainly liquid crystal SLM (acronym for "Spatial Light Modulators") and DM (acronym for Deformable Mirrors). Such devices are also limited in their ability to refresh at high rate the modulation pattern, in most of the cases in the range of a few Hertz (Hz) to a few kilohertz (kHz).

In the case of the scanning in three dimensions of a single spot, it is also known from the article by Reddy et al. entitled "*Three-dimensional random access multiphoton microscopy for functional imaging of neural activity*" published in Nature Neuroscience, 11, 713-720 (2008) to achieve three-dimensional ultra-fast scanning using a system involving four acousto-optic deflectors.

Acousto-optic deflectors (often named after their acronym AOD) are fast pointing devices based on the interaction between an acoustic compression or shear wave propagating in a crystal and an electromagnetic wave. In most cases, the electromagnetic wave has a planar or a spherical wavefront. If a fixed frequency wave is used in an acousto-optic deflector, the resulting diffractive process deflects a fraction of the electromagnetic wave at an angle proportional to the acoustic frequency of the acoustic wave. The use of linearly chirped acoustic wave in the acousto-optical deflector, as described in the article by Reddy et al., allows creating a cylindrical lens in the acousto-optic deflector, whose focal length is inversely proportional to the chirp rate.

The system described in the Reddy et al. article, which contains four acousto-optic deflectors, implies strong loss of light power because the diffraction efficiency in an acousto-optic deflector is limited even in its optimal configuration. In addition, the third and the fourth acousto-optic deflectors of the system cannot be used in their optimal configuration (Bragg incidence), which also contributes to increased loss of light power in the system. Finally, the linear frequency chirps have to be stopped each time they reach the limit of the frequency bandwidth of the acousto-optical deflector, thus limiting the dwell time on the points accessed in three dimensions and the useful fraction of the duty cycle. Finally, such system is limited to the scanning in three dimensions of a single spot and cannot be used to create spatially extended light patterns.

It is also known from document DE 10 2013 201 968 a device which has a radiation source generating a pulsed, electro-magnetic radiation. A photodetector is used for temporal detection of radiation pulses. A signal source is coupled with the photodetector for precise trigger of sound waves generation. An acousto-optical deflector is driven by the signal source with a frequency-modulated control signal such that sound waves and radiation are linked in time. In this implementation refractive and/or diffractive beam transformation and/or beam deflection of the radiation is/are performed at the time of passage of the radiation through the deflector.

SUMMARY OF THE INVENTION

The invention aims at solving the problems of the known systems with a new system for generating a light pattern (three-dimension scans and spatially extended light patterns), which is able to operate at a high speed.

To this end, the invention concerns a method for analyzing a sample with a non-linear microscopy technique, in particular two-photon fluorescence microscopy, the method comprising at least the following steps:
  a) emitting at least one input laser pulse having a duration below or equal to 10 picoseconds,
  b) deflecting the input laser pulse in a first direction by a first acousto-optical deflector to obtain a first deflected laser pulse,
  c) deflecting the first deflected laser pulse in a second direction by a second acousto-optical deflector to obtain a second deflected laser pulse, the first direction and the second direction defining at least an angle comprised between 85° and 95°, and
  d) sending the second deflected laser pulse on an optic system, to obtain a desired pattern of light within the sample,
characterized in that:
  each acousto-optic deflector comprises an acousto-optical crystal and a transducer adapted to command the crystal by applying an acoustic wave, the instant when step a) is carried out and the instants at which the time-varying acoustic wave commands are started in the acousto-optic deflectors being synchronized such that each acousto-optic deflector only interacts with a laser pulse when the acoustic wave is established in the crystal,
  at step b), the first acousto-optical deflector further shapes spatially the first deflected pulse in phase and in amplitude according to a first function,
  at step c), the second acousto-optical deflector further shapes spatially the second deflected laser pulse in phase and in amplitude according to a second function, and both the first function f and the second function g are such that at step d), the desired pattern of light is obtained by holography through the optic system.

By focusing, with an optical system as for example a lens, the method enables to achieve:

the 3D scanning of a single point near the focus. Axial scanning can be achieved using phase modulation only, without amplitude modulation: either using simple quadratic phase profile, or using more complex phase profile including compensation of the aberrations introduced by the objective when it is used to focus light far from its focal plane (Botcherby Optics Communications 281 (2008) 880-887), and compensation of sample-induced aberrations using a phase profile determine by any adaptive optical methods.

the creation of spatially extended light pattern near the lens focal plane. This includes the creation of multiple points and/or the sculpting of extended spatial intensity profile. Both phase and amplitude modulations are in principle needed. The amplitude and phase profiles defined by the product of the two functions is computed and/or optimized to obtain the targeted light intensity pattern using published methods and algorithms (Golan et al., J. Neural Eng. 6 (2009) 066004). Due to the geometry of the modulation created by the acousto-optical-deflectors, the resulting extended light patterns that can be generated will also be the product of a function along one direction by a function along the second direction.

Thanks to the invention, arbitrary pattern of light can thus be generated at a high speed and scanned in three dimensions in a target focal volume. In addition, as only two acousto-optic deflectors are involved, the loss of light power is reduced. Therefore, such method is applicable even for highly scattering tissues, when high laser power is required.

According to further aspects of the invention that are advantageous but not compulsory, the method might incorporate one or several of the following features, taken in any technically admissible combination:

the first function and the second function are further chosen to introduce a desired spatial modulation of the amplitude and phase in the second deflected pulse.

the first function and the second function are further chosen to achieve three-dimension scanning of the sample.

step a) is carried out by using a laser unit comprising a femtosecond pulsed laser and a regenerative amplifier.

the method further comprises a step e) of emitting a first time-varying radiofrequency wave to command the first acousto-optical deflector, step e) being carried out before step a).

the interval of time between the instant when step e) is carried out and the instant when step a) is carried out is comprised between 1 and 30 microseconds.

the method further comprises the following steps:
e) emitting a first time-varying radiofrequency wave to command the first acousto-optical deflector, and
f) emitting a second time-varying radiofrequency wave to command the second acousto-optical deflector.

the instant when step e) is carried out and the instant when step f) is carried out are determined with a precision below or equal to 200 nanoseconds, relative to the instant when the laser pulse is emitted.

steps e) and f) are carried out, so that the first radiofrequency wave in the first acousto-optic deflector and the second radiofrequency wave in the second acousto-optic deflector are established simultaneously in the first and second acousto-optic deflectors.

the second deflected laser pulse has a spatial and/or temporal dispersion, the method further comprising a step of compensating for the spatial and/or temporal dispersion of the second deflected laser pulse.

the method further comprises a step of determining the first function and the second function.

each acousto-optic deflector has an access time and wherein at step a), several laser pulses are emitted at a repetition rate inferior or equal to the inverse of the largest of these access times.

the sample is adapted to tolerate an exposition to a maximum repartition of intensity of light in the focal plane, the method further comprising choosing the desired pattern of light so that the repartition of the intensity of the desired pattern of light in the focal plane be inferior to the maximum repartition of intensity.

The invention also relates to a non-linear microscope, comprising a system for generating at least a desired pattern of light, the system comprising:

a laser unit adapted to emit at least one input laser pulse having a duration below or equal to 10 picosecond, a first acousto-optical deflector adapted to deflect a laser pulse in a first direction to obtain a first deflected laser pulse, a second acousto-optical deflector adapted to deflect the first deflected laser pulse in a second direction to obtain a second deflected laser pulse, the first direction and the second direction defining at least an angle comprised between 85° and 95°, and an optic system adapted to send the second deflected laser pulse, to obtain a desired pattern of light within the sample, characterized in that:

each acousto-optic deflector comprises an acousto-optical crystal and a transducer adapted to command the crystal by applying an acoustic wave, the laser unit and the acousto-optical deflectors being synchronized such that each acousto-optic deflector only interacts with a laser pulse when the spatial pattern of acoustic wave is established at the appropriate coordinates in the crystal optic window the first acousto-optical deflector is further adapted to spatially shape the first deflected laser pulse in phase and in amplitude according to a first function, the second acousto-optical deflector is further adapted to spatially shape the second deflected laser pulse in phase and in amplitude according to a second function, and both the first function f and the second function g are such that the desired pattern of light is obtainable by holography through the optic system.

According to another embodiment, the laser unit comprises a femtosecond pulsed laser and a regenerative amplifier.

According to an embodiment, the non-linear microscope is a two-photon microscope.

BRIEF DESCRIPTION OF THE DRAWINGS

The invention will be better understood on the basis of the following description, which is given in correspondence with the annexed figures and as an illustrative example, without restricting the object of the invention. In the annexed figures:

FIG. 3 is a side view of the part of the laser scanning unit represented in FIG. 2.

DETAILED DESCRIPTION OF SOME EMBODIMENTS

For the remainder of the description, a longitudinal direction is defined: the longitudinal direction corresponds to the general direction of the propagation of light. Two transversal directions perpendicular to the longitudinal direction are also defined, the first transversal direction being further perpendicular to the second transversal direction. The longitudinal and transversal directions are respectively symbolized by an axis Z and axes X and Y on FIGS. 1 to 3.

Figure 1:
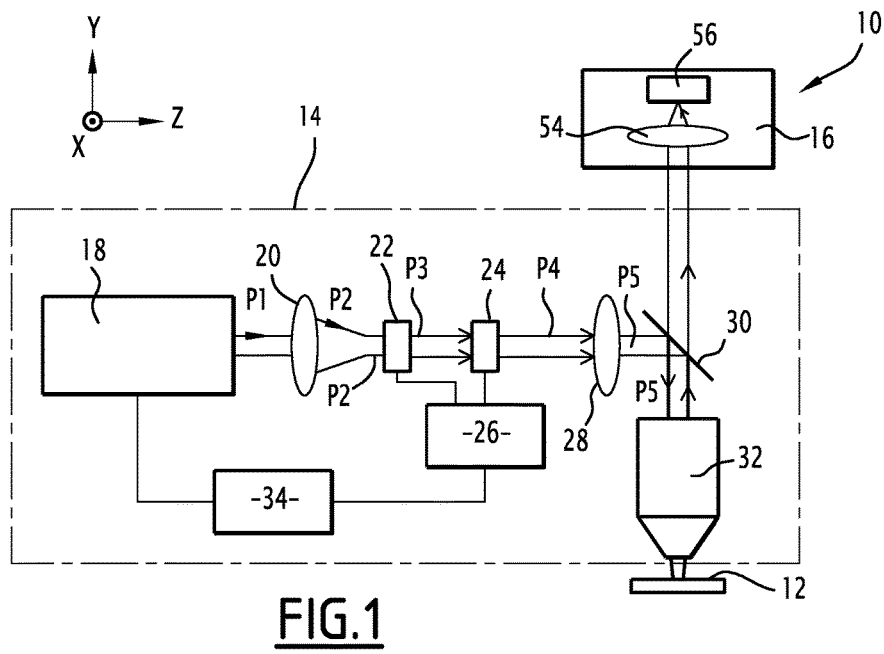
FIG. 1 is a schematic representation of a two-photon microscope according to the invention comprising a system for generating a light pattern according to the invention.

A two-photon microscope 10 adapted to achieve a two-photon microscopy on a sample 12 is represented on FIG. 1.

Alternatively, the microscope 10 may be any microscope able to achieve a non-linear microscopy technique. Such microscope is called a non-linear microscope.

The sample 12 is, for instance, a soft tissue. In the meaning of the present invention, a soft tissue is an organic tissue, which can have an animal or vegetal origin. For instance, such a soft tissue can be a muscle or any portion of a human body, of an animal body or of a vegetable. A soft tissue can also be a non-metallic part of a prosthesis.

The microscope 10 comprises a system 14 for generating at least a desired pattern of light and a detecting unit 16.

The system 14 for generating at least a desired pattern of light comprises a laser unit 18, a first optical system 20, a first acousto-optical deflector 22, a second acousto-optical deflector 24, a radiofrequency generator 26 for both acousto-optical deflectors 22, 24, a second optical system 28, a beam splitter 30, an optical system 32 and a controller unit 34.

System 14 is adapted to generate a three-dimensional scan of a point in the sample 12. It is also adapted to generate a desired spatially extended pattern of light in the sample 12, which is different from a point. For instance, a spatially extended light pattern is a square or four points arranged spatially so as to form a square. Preferably, in the frame of this invention, the light patterns considered can be written as the product of two distinct functions, corresponding to the product of two distinct modulation functions created by the two acousto-optical deflectors 22, 24. Indeed, such kind of light patterns is more easily generated than arbitrary patterns.

The laser unit 18 is adapted to emit at least one laser pulse having a duration below or equal to 1 nanosecond. The pulse duration is typically in the range of some picoseconds or less.

The laser unit 18 comprises a laser source. The laser source is adapted to emit a coherent light whose wavelength is comprised between 400 nanometers (nm) and 2 micrometers (μm). The laser source is preferably a femtosecond pulsed laser adapted to emit laser pulses with a duration comprised between 10 fs and 10 picoseconds (ps).

Preferably, the femtosecond laser is adapted to emit laser pulses with a full width at half maximum strictly inferior to 10 picoseconds.

Alternatively, the laser unit 18 also comprises an element of spatial and/or temporal precompensation of the pulses emitted by the laser source. Such element is, for example, a prism, a grating or another acousto-optical deflector.

According to a preferred embodiment, the laser unit 18 also comprises a regenerative amplifier. A regenerative amplifier is a device which is used for obtaining a relatively strong amplification of optical pulses, usually with ultrashort pulse durations in the picosecond or femtosecond domain. In this embodiment, the laser unit 18 is thus adapted to provide optical pulses with relatively high intensity. For imaging applications, energy per pulse up to a few μJ are convenient.

The first optical system 20 is adapted to make the laser pulse emitted by the laser unit 18 going towards the first acousto-optical deflector 22.

The first acousto-optical deflector 22 is adapted to deflect an input beam in the first transverse direction X to obtain a first deflected beam. In other words, the first acousto-optical deflector 22 is adapted to carry out a scan of the sample 12 in the first transverse direction X.

The first acousto-optical deflector 22 comprises a first acousto-optical crystal 36, a first transducer 38 and a first casing 40 protecting the first acousto-optical crystal 36.

The first acousto-optical crystal 36 has a parallelepipedic shape, the light entering by a first input face 362 and leaving by a first output face 364.

The distance between the first input face 362 and the first output face 364 along the longitudinal direction Z is the thickness of the crystal.

The first acousto-optical crystal 36 is a crystal made in $TeO_2$. Any other material exhibiting acousto-optical properties may be considered.

The first transducer 38 is adapted to command the first acousto-optical crystal 36 by applying a first acoustic wave. The variation of the properties of the first acoustic wave with time is according to a first law of command L1. Such properties comprise, for instance, the amplitude, the phase and the frequency of the first acoustic wave.

The first acousto-optical deflector 22 is further adapted to spatially shape the first deflected laser pulse in phase and in amplitude according to a first complex function f. It can be shown that the first function f can be expressed as a function of a coordinate along the first transverse direction X. For the remainder of the description, this coordinate is labeled x.

The second acousto-optical deflector 24 is adapted to deflect the first deflected beam in the second transverse direction Y to obtain a second deflected beam. In other words, the second acousto-optical deflector 24 is adapted to carry out a scan of the sample 24 in the second transverse direction Y.

The first transverse direction X and the second transverse direction Y define at least an angle α comprised between 85° and 95°.

Figure 2:
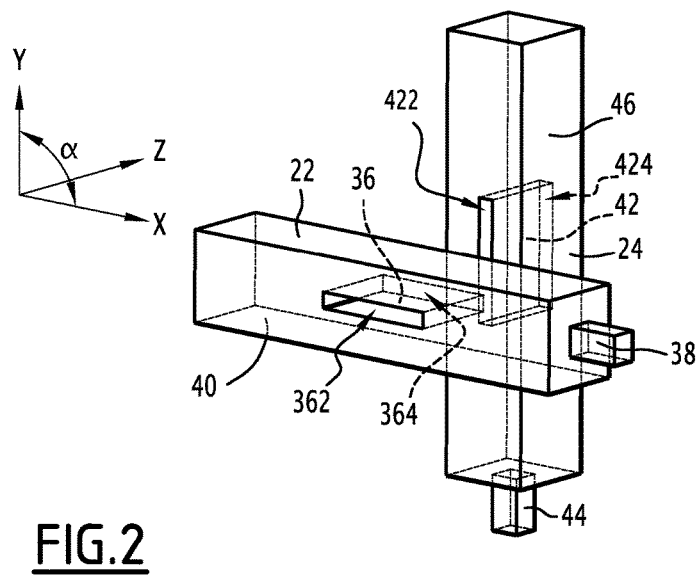
FIG. 2 is a perspective view of a part of the system for generating a light pattern of FIG. 1.

Preferably, as can be seen on FIGS. 1 to 3, the angle α is equal to 90°. Such configuration for the two acousto-optical deflectors 20, 24 is named a "crossed" configuration.

The second acousto-optical deflector 24 comprises a second acousto-optical crystal 42, a second transducer 44 and a second casing 46 protecting the second acousto-optical crystal 42.

The second acousto-optical crystal 42 has a parallelepipedic shape, the light entering by a second input face 422 and leaving by a second output face 424.

The distance between the second input face 422 and the second output face 424 along the longitudinal direction Z is the thickness of the crystal.

In the specific case illustrated, the second acousto-optical crystal 42 is identical to the first acousto-optical crystal 36.

The optical distance d between the first acousto-optical crystal 36 and the second acousto-optical crystal 42 along the longitudinal direction Z is inferior to 30 millimeters (mm). This enables to limit the astigmatism of the lensing effect generated by the use of both acousto-optical deflectors 22, 24. By definition, the optical distance d is the distance between the first output face 364 and the second input face 422 in the absence of optical relay system.

In case an optical relay system is present, this optical relay images the first output face 364 into a conjugate plane and the optical distance d12 is the distance from this image plane to the second input face 422.

According to a preferred embodiment of the invention, the optical distance d is inferior to 15 millimeters (mm).

The second transducer 44 is adapted to command the second acousto-optical crystal 42 by applying a second acoustic wave. The variation of the properties of the second acoustic wave with time is according to a second law of command L2. Such properties comprise, for instance, the amplitude, the phase and the frequency of the second acoustic wave.

The second acousto-optical deflector 24 is further adapted to spatially shape the second deflected laser pulse in phase and in amplitude according to a second complex function g. It can be shown that the second function g can be expressed as a function of a coordinate along the second transverse direction Y. For the remainder of the description, this coordinate is labeled y.

In an alternative embodiment, both acousto-optical crystals 40, 42 are in the same casing.

The radiofrequency generator 26 for both acousto-optic deflectors 22, 24 is adapted to provide, to each transducer 38, 44, radiofrequency waves. Each transducer 38, 44 is adapted to convert radiofrequency waves in an acoustic wave. Thus, the radiofrequency generator 26 is able to provide a first sequence of radiofrequency waves to the first transducer 38 corresponding to the first law of command L1. The radiofrequency generator 26 is also able to provide a second time-dependent radiofrequency wave to the second transducer 44 corresponding to the second law of command L2.

The radiofrequency generator 26 is a direct digital synthesizer. Such device (whose usual acronym is DDS) is a type of frequency synthesizer used for creating arbitrary waveforms from a single, fixed-frequency reference clock.

Alternatively, the radiofrequency generator 26 is an analog system.

The second optical system 28 is adapted to serve as an optical relay between the output of the second acousto-optical deflector 24 and the optical system 32. The second optical system 28 is, for instance, a 4f relay.

The beam splitter 30 is adapted to reflect the light issued from the second acousto-optical deflector 24 towards the optical system 32 and to transmit the light collected by the optical system 32 to the detecting unit 16. For instance, the beam splitter 30 is a dichroic mirror.

The optical system 32 is, in the case of FIG. 1, an objective 32. Alternatively, the optical system 32 is any combination of lenses.

The objective 32 is adapted to make the light received from the beam splitter 30 converge on a focal point situated in the vicinity of its focal plane located in the sample 12, to gather light emitted by the sample 12 and to send it to the beam splitter 30.

The objective 32 is an air objective, an oil-immersion objective or water-immersion objective comprising a combination of several optical elements. The objective 32 provides a magnification usually ranging from 10 to 100, when used with its associated tube lens, and a numerical aperture comprised between 0.5 and 1.4.

The controller unit 34 is adapted to synchronize the laser pulse unit 18 and the radiofrequency generator 26 such that each pulse emitted by the laser pulse unit 18 interacts with both acousto-optic deflectors 22, 24 when respectively the first acoustic wave and the second acoustic wave have the spatial profile in the optic windows of the two acousto-optic deflectors 22, 24 enabling to obtain the desired pattern of light.

The detecting unit 16 comprises a third optical system 54 and a detector 56. The third optical system 54 is adapted to collect the light transmitted by the beam splitter 30 and to focus it on the detector 56. The detector 56 is adapted to convert the light received in an electrical signal. The detector 56 is, for instance, a photomultiplier.

Operation of the microscope 10 for two-photon imaging is now described when it is desired to obtain a desired pattern of light.

At a first instant t1, the radiofrequency generator 26 start to apply a first radiofrequency wave to command the first acousto-optical deflector 22. The first transducer 38 converts the first radiofrequency wave into a first acoustic wave, which propagates in the first crystal 36 and along the first transverse direction X. This first acoustic wave has time-dependent amplitude and frequency, given by two first functions of time, with a continuity of the phase of the wave (these functions constitute together the first law of command L1). The resulting spatial profile of this first acoustic wave in the first crystal 36 at the time when the optical wave interacts with the first acousto-optical deflector 22, is such that the optical wave is spatially shaped in phase and in amplitude according to the first function f. The establishment time of the first acoustic wave in the first crystal 36, that is the interval between the instant t1 when the acoustic wave command is generated and the instant $t1+t_{access,1}$ when the acoustic wave reaches the extremity opposite to the transducer of the optical window of the AOD, is referred as the access time $t_{access,1}$ of the first acousto-optical deflector 22. The access time notably depends from the size of the crystal along the axis X of propagation of the acoustic wave and from the frequency of the acoustic wave.

At a second instant t2, the radiofrequency generator 26 starts to apply a second radiofrequency wave to command the second acousto-optical deflector 24. The second transducer 44 converts the second radiofrequency wave into a second acoustic wave which propagates in the second crystal 42 and along the second transverse direction Y. This second acoustic wave has time-dependent amplitude and frequency, given by two second functions of time, with a continuity of the phase of the wave (these functions constitute together the second law of command L2). The resulting spatial profile of this second acoustic wave in the second crystal 42 at the time when the optical wave interacts with the second acousto-optical deflector 24, is such that the optical wave is spatially shaped in phase and in amplitude according to the second function g. The establishment time of the second acoustic wave in the second crystal 42, that is the interval between the instant t2 when the acoustic wave command is generated and the instant $t2+t_{access,2}$ when the acoustic wave reaches the extremity opposite to the transducer of the optical window of the AOD, is referred as the access time $t_{access,2}$ of the second acousto-optical deflector 22.

Both the precision in the determination of the first instant t1 and the precision in the determination of the second instant t2 are below or equal to 200 nanoseconds.

Preferably, the first instant t1 and the second instant t2 are chosen so that the first radiofrequency wave and the second radiofrequency wave are established simultaneously in the first and second acousto-optic deflectors (t1+$t_{access,1}$= t2±$t_{access,2}$)

The synchronization between the first instant t1 and the second instant t2 is carried out by the controller unit 34 and takes into account all the delays in the establishments of the two radiofrequency waves in the two acousto-optic deflectors 22, 24.

At a third instant t3, the laser unit 18 emits a first laser pulse P1 towards the first optical system 20. The third instant t3 is posterior to the first instant t1.

More precisely, the third instant t3 is chosen so that the second laser beam pulse P2 interacts with the first acousto-optical deflector 22 when the first acoustic wave is established in the first acousto-optical 36. In other words, the interval of time between the first instant t1 and the third instant t3 is equal to the access time of the first acousto-optical deflector 22 (t3=t1±$t_{access,1}$) Therefore, the interval of time between the first instant t1 and the third instant t3 is comprised between 2 and 50 microseconds.

Such synchronization between the first instant t1 and the third instant t3 is carried out by the controller unit 34.

Both the precision in the determination of the first instant t1 and the precision in the determination of the third instant t3 are below or equal to 200 nanoseconds.

Then, the first optical system 20 converts the first laser pulse P1 into a second laser pulse P2 whose waist is located in the first acousto-optical deflector 22. The second laser pulse P2 can thus be considered as the input laser pulse for the first acousto-optical deflector 22.

The first acousto-optical deflector 22 deflects the second laser pulse P2 by a first angle of deviation in the first transverse direction X. This first deflected pulse is labeled P3. The first acousto-optical deflector 22 simultaneously spatially shapes the input laser pulse P2 in phase and amplitude in accordance with the first function f.

The first deflected pulse P3 propagates towards the second acousto-optical deflector 24. The second acousto-optical deflector 24 deflects the first deflected pulse P3 by a second angle of deviation in the second transverse direction Y. This second deflected pulse is labeled P4. The second acousto-optical deflector 24 simultaneously spatially shapes the first deflected laser pulse P3 in phase and amplitude in accordance with the second function g.

The spatial modulation W4 of the second deflected laser pulse P4 is the product of the first function f with the second function g. Due to the fact that the first function f depends only from x and the second function g depends only from y, the spatial modulation produced by the system 14 has the form of the product of a function of x by a function of y. Therefore, the amplitude modulation is the product of a function of x by a function of y. The phase modulation is the sum of a function of x and a function of y.

The second deflected beam P4 then propagates towards the objective 32 via the second optical system 28 which serves as a relay and reflects on the beam splitter 30, so as to obtain a fifth laser pulse P5 whose spatial modulation W5 is similar to the spatial modulation W4.

The objective 32 makes the fifth laser pulse P5 convergent near the focal plane located in the sample 12. By the expression "near", it is meant that the distance is inferior to 1 mm. The intensity distribution near the focal plane is determined by the spatial modulation W5.

More precisely, in the context of the invention, both the first function f and the second function g enables to obtain by holography through the objective 32 the desired pattern of light in the image space of the objective 32.

Different type of light pattern can be obtained by this method. Different cases are listed below:
A) Single spot scanning in three dimensions.
  1. By creating a spatial modulation W5 with a phase modulation only and reduced to tip, tilt and defocus, light can be focused to a single spot positioned at a given position in three dimensions near the objective focus. If the tip, tilt and defocus of the wavefront are varied in time, a three dimensional scan of the sample is achieved at either discrete or contiguous positions.
  2. Aberrations due to the use of the objective out of its focal plane or due to the sample structure can be corrected by using a spatial modulation W5 with a more complex phase modulation. Spherical aberration of the objective out of its focal plane can be compensated using the phase given in Eq. 9 of the following publication (Botcherby Optics Communications 281 (2008) 880-887). As this phase is not a simple sum of a function of x and a function of y, only an approximation will be used. Tissue-induced aberrations will be compensated by applying a phase modulation W5 obtained by any method of adaptive optics. The applied phase will be an approximation of the optimal phase due to the fact that only phase modulation being a sum of a function of x and a function of y can be generated.
B) Spatially extended light pattern.
  1. Two-dimensional spatially extended light pattern can be created in the focal plane of the sample. In that case, the intensity distribution in the focal plane is the square of the modulus of the Fourier transform of the spatial modulation W5 of the fifth laser pulse P5. Mathematically, this implies the following relations:

$$OF(x,y)=|FT(W_5(w,y))|^2=|FT(f(x)\cdot g(y))|^2=|FT(f(x))\cdot FT(g(y))|^2$$

where:
  The two-dimensional pattern of light may be expressed in term of a targeted optical function OF. OF is a function of the coordinates x and y in the focal plane of the objective 32, and
  FT is the Fourier transform.
  Therefore, a light pattern is obtained in the focal plane. This includes the creation of multiple points and/or the sculpting of extended spatial intensity profile. The functions f(x) and g(y) can be obtained from the target intensity distribution OF using published methods and algorithms (Golan et al., J. Neural Eng. 6 (2009) 066004). In this optimization, either phase only or phase and amplitude modulation can be used to target the desired light pattern.
  2. Spatially extended light pattern can be addressed in three dimensions by combining the cases A and B, by adding the phase modulation for scanning a point in three dimensions to the phase and/or amplitude modulation to generate a extended spatial light pattern in the focal plane.

As two-photon microscopy relies on the two-photon absorption phenomena predicted by Goeppert-Mayer in 1931, at each point of the light pattern, an interaction between the sample 12 and light occurs by simultaneous absorption of pairs of photons of the fifth laser pulse F5 by the sample 12. Following most of these biphotonic absorption events, the sample 12 emits one photon by fluorescence.

The wavelength of the photon emitted is larger than half the wavelength of the photons of one pair.

Other applications include non-linear microscopy techniques, such as three-photon excitation fluorescence, second harmonic generation and third-harmonic generation microscopy, as well as physical (e.g. ablation) and chemical (e.g. photobleaching, photopolymerization, uncaging, photoactivation) modifications of the sample.

The objective 32 then gathers the fluorescence light emitted by the sample 12.

The beam splitter 30 transmits the fluorescence light towards the detecting unit 16.

The third optical system 54 makes the fluorescence light converge on the detector 56, which converts the fluorescence light in an electrical signal. This electrical signal contains information relative to the arrangement of sample 12 in space. Based on the electrical signal, a measure of the fluorescence intensity of the sample 12 at the position of the light pattern at this instant is achieved. Such measurement can be repeated over a given duration either at the same position, or over different discrete positions in two-dimension or three-dimension or over a set of continuous positions in two-dimension or three-dimension to analyze the sample 12.

Therefore, the system 14 for generating at least a desired pattern of light enables to achieve an arbitrary pattern in a plane with a rate of up to 500 kHz. Indeed, at the time a pulse crosses one of the acousto-optical deflector 22, 24, this pulse interacts with a fixed acoustic grating generated by a controlled acoustic wave. The evolution of the properties of such acoustic waves with time, given by the laws of commands L1 and L2, are chosen to obtain the desired pattern. For this, for instance, the controller unit 34 determines the first function f and the second function g based on the desired pattern of light.

Let's consider an incident pulse propagating along the longitudinal direction Z and interacting with the first acousto-optical deflector 22.

Thus, the complex amplitude of the incident pulse can be expressed as:

$$A_{in}(x,y,z) = A_{in}(x,y) e^{i(k_0 z + \varphi_0(x,y))}$$

where:
- $A_{in}(x, y, z)$ is the complex amplitude of the incident pulse,
- z is the coordinate along the longitudinal axis Z,
- $k_o$ is the wavevector of the incident pulse,
- $A_{in}(x,y)$ is the incident amplitude profile of the incident pulse. The amplitude profile is, for instance, planar or Gaussian.
- $\varphi_{in}(x,y)$ is the incident wavefront of the incident pulse. Preferably, the incident wavefront $\varphi_{in}(x,y)$ is planar for optimizing diffraction efficiency in the first acousto-optical crystal 40.

When the first acousto-optical deflector 22 is fed with an ultrasonic wave with frequency FREQ(x) and amplitude $a_1(x)$ at a position x in the first acousto-optical deflector 22, after interaction, the complex amplitude of the deflected pulse can be expressed as:

$$A_{out}(x,y,z) = A_{in}(x,y) \cdot T_1(a_1(x)) e^{i(k_0 z + \varphi_0(x,y) + \varphi_1(x))}$$

Where:
- $A_{out}(x, y, z)$ is the amplitude of the deflected pulse,
- $\varphi_1(x,y)$ is the phase shift introduced by the first acousto-optical deflector 22 between the deflected laser pulse and the incident laser pulse.
- $T_1$ is the characteristic input-output amplitude transfer function of the first acousto-optical deflector (22) expressing the fraction of the input light amplitude transferred into the first diffraction order, as a function of the acoustic wave amplitude $a_1$.

The spatial modulation f of the incident optical wave created by the first acousto-optical deflector 22 is therefore given by:

$$f(x) = T_1(a_1(x)) e^{i\varphi_1(x)}$$

The phase shift $\varphi_1(x,y)$ introduced by the first acousto-optical deflector 22 between the deflected laser pulse and the incident laser pulse is related to the frequency FREQ(x) of the ultrasonic wave in a complex manner.

At each point x of the AOD, the rays are diffracted in a direction given by:

$$\theta(x) = \frac{\lambda \cdot FREQ(x)}{v}$$

At any point x, the rays coming out of the first acousto-optical deflector 22 are perpendicular to the wavefront. Therefore, the optical path difference between the position x and x+dx of the wavefront due to the angle θ(x) of the rays at the coordinated x, is θ(x).dx and the wavefront is therefore related to the frequency in the acousto-optic deflector by:

$$\frac{d\phi_1(x)}{dx} = \frac{2\pi}{\lambda} \theta(x) = \frac{2\pi \cdot FREQ(x)}{v}$$

This can be written as the following equations:

$$\phi_1(x) = \frac{2\pi}{v} \int_{x_0}^{x} FREQ(u) du$$

$$\phi_1(x) = \frac{2\pi}{v} \left[ uFREQ(u) \right]_{x_0}^{x} - \int_{x_0}^{x} uFREQ'(u) du$$

$$\phi_1(x) = \frac{2\pi}{v} \left( xFREQ(x) - x_0 FREQ(x_0) - \int_{x_0}^{x} uFREQ'(u) du \right)$$

where $x_0$ is the coordinate of the position of the extremity opposite to the transducer of the optical window of the first acousto-optical crystal 40 along the first transverse direction X.

In this expression $FREQ(x_0)$ is generated at time t1, FREQ(x) is generated at time $t1+(x-x_0)/v$, and $\varphi(x)$ is obtained at time $t1+t_{access,1}$, $t_{access,1}$ being the access time of the first acousto-optic deflector, i.e. the interval between the instant t1 when the acoustic wave command is generated and the instant $t1+t_{access,1}$ when the acoustic wave reaches the extremity opposite to the transducer of the optical window of the first acousto-optic deflector, This expression shows that the phase profile created at a position x, for a single acousto-optical deflector cannot be related only to the ultrasonic frequency at the pixel x in the acousto-optical deflector but is related to the whole ultrasonic pattern from an extremity to the point x.

By applying successively such reasoning to each acousto-optical deflector, the spatial modulation g of the incident optical wave created by the second acousto-optical deflector 24 is therefore given by:

$$g(Y) = T_2(a_2(y)) e^{i\varphi_2(u)}$$

Therefore, this configuration can create phase and amplitude modulations having the functional form of $T_1(a_1(x)) \cdot T_2(a_2(y)) \exp[i\varphi_1(x)+\varphi_2(y))]$, where $T_1(a_1(x))$ and $T_2(a_2(y))$ are the amplitude modulation created respectively by the first and second acousto-optic deflector 22, 24 and $\varphi_1(x)$ and $\varphi_2(y)$ are the phase modulation created respectively by the first and second acousto-optic deflector 22, 24.

By definition, the evolution of the respective amplitude and the respective frequency of each acoustic wave with time is included in the respective law of commands L1 and L2. Thus, the first function f and the second function g enable to deduce laws of commands L1 and L2 appropriate to obtain the desired pattern.

Furthermore, the system 14 is easy to implement since only two acousto-optical deflectors 22, 24 are involved. This results in a relatively high excitation power for the fifth laser pulse P5. Such high excitation power renders the system 14 particularly adapted to produce non-linear effects, such as two-photon fluorescence absorption, second harmonic generation, third harmonic generation or coherent anti-Raman scattering. In addition such non-linear experiments may be carried out on highly scattering tissues at large depths.

Additionally, although the system 14 for generating at least a desired pattern of light has been presented for an application related to two-photon fluorescence microscopy, the system 14 can also be used for any measurement in the vicinity of the focal plane, such as transmission, fluorescence, refraction, polarization, scattering or reflection. In such cases, the beam splitter 24 may not be present and the detector unit 28 may be different.

According to another embodiment, the light pattern evolves with time. In this case, several laser pulses are emitted by the laser unit 18 at a repetition rate. Such repetition rate should be inferior or equal to the inverse of the largest of the access times of the two acousto-optic deflectors 22, 24.

According to another embodiment, the lensing effect generated by both acousto-optic deflectors 22, 24 is used to modify the position of the focal plane in the sample 12 along the longitudinal direction Z. In this way, a three-dimensional scanning of the sample 12 is obtained.

For instance, each law of command L1 and L2 also imposes a linear variation of frequency with time of the respective acoustic waves to which they are associated. In this case, the lensing effect generated by both acousto-optical deflectors 22, 24 is equivalent to a spherical lens having a non-zero power. This equivalence is more and more exact as the distance d between the two crystals 36, 42 gets smaller. This power causes an axial displacement of the focal plane in the sample 12 along the longitudinal direction Z.

Such three-dimensional scanning can be performed at a refresh rate of up to 500 kHz.

According to another embodiment, as the second deflected laser pulse has a spatial and/or temporal dispersion, the system comprises a unit for compensating for the spatial and/or temporal dispersion. Such unit for compensating for the spatial and/or temporal dispersion is, for instance, a prism, a grating, a pair of prisms or another acousto-optic device.

According to another embodiment, notably if the laser unit 18 comprises a laser and a regenerative amplifier, the repartition of the intensity of the desired pattern of light depends on the sample analyzed so as to avoid any damage to the sample. A sample is adapted to tolerate the exposition to a maximum repartition of intensity of light in the focal plane if such intensity of light does not alter the sample in a permanent way. The example given here above concerns a two-photon microscopy technique. The person skilled in the art understands that the present invention may easily be transposed for any kind of non-linear microcopy technique.

As an example, if the sample is adapted to tolerate an exposition to a maximum repartition of intensity of light in the focal plane, the desired pattern of light is chosen so that the repartition of the intensity of the desired pattern of light in the focal plane is inferior to the maximum repartition of intensity.

The embodiments and alternative embodiments considered here-above can be combined to generate further embodiments of the invention.

The invention claimed is:

1. Method for analyzing a sample with a non-linear microscopy technique, in particular two-photon fluorescence microscopy, the method comprising at least the following steps:
    a) emitting at least one input laser pulse having a duration below or equal to 10 picoseconds,
    b) deflecting the input laser pulse in a first direction by a first acousto-optical deflector to obtain a first deflected laser pulse, and
    c) deflecting the first deflected laser pulse in a second direction by a second acousto-optical deflector to obtain a second deflected laser pulse, the first direction and the second direction defining at least an angle comprised between 85° and 95°,
    d) sending the second deflected laser pulse on an optic system, to obtain a desired pattern of light within the sample,
    characterized in that:
        each acousto-optic deflector comprises an acousto-optical crystal and a transducer adapted to command the crystal by applying an acoustic wave, the instant when step a) is carried out and the instants at which the time-varying acoustic wave commands are started in the acousto-optic deflectors being synchronized such that each acousto-optic deflector only interacts with a laser pulse when the acoustic wave is established in the crystal,
        at step b), the first acousto-optical deflector further shapes spatially the first deflected pulse in phase and in amplitude according to a first function,
        at step c), the second acousto-optical deflector further shapes spatially the second deflected laser pulse in phase and in amplitude according to a second function, and
        both the first function f and the second function g are such that at step d), the desired pattern of light is obtained by holography through the optic system.

2. A method according to claim 1, wherein the first function and the second function are further chosen to introduce a desired spatial modulation of the amplitude and phase in the second deflected pulse.

3. A method according to claim 2, wherein the first function and the second function are further chosen to achieve three-dimension scanning of the sample.

4. A method according to claim 1, wherein step a) is carried out by using a laser unit comprising a femtosecond pulsed laser and a regenerative amplifier.

5. A method according to claim 1, wherein the method further comprises a step e) of emitting a first time-varying radiofrequency wave to command the first acousto-optical deflector, step e) being carried out before step a).

6. A method according to claim 5, wherein the interval of time between the instant when step e) is carried out and the instant when step a) is carried out is comprised between 1 and 30 microseconds.

7. A method according to claim 1, wherein the method further comprises the following steps:
  e) emitting a first time-varying radiofrequency wave to command the first acousto-optical deflector, and
  f) emitting a second time-varying radiofrequency wave to command the second acousto-optical deflector,
and wherein the instant when step e) is carried out and the instant when step f) is carried out are determined with a precision below or equal to 200 nanoseconds, relative to the instant when the laser pulse is emitted.

8. A method according to claim 7, wherein steps e) and f) are carried out, so that the first radiofrequency wave in the first acousto-optic deflector and the second radiofrequency wave in the second acousto-optic deflector are established simultaneously in the first and second acousto-optic deflectors.

9. A method according to claim 1, wherein the second deflected laser pulse has a spatial and/or temporal dispersion, the method further comprising a step of compensating for the spatial and/or temporal dispersion of the second deflected laser pulse.

10. A method according to claim 1, wherein the method further comprises a step of determining the first function and the second function.

11. A method according to claim 1, wherein each acousto-optic deflector has an access time and wherein at step a), several laser pulses are emitted at a repetition rate inferior or equal to the inverse of the largest of these access times.

12. A method according to claim 1, wherein the sample is adapted to tolerate an exposition to a maximum repartition of intensity of light in the focal plane, the method further comprising choosing the desired pattern of light so that the repartition of the intensity of the desired pattern of light in the focal plane be inferior to the maximum repartition of intensity.

13. A non-linear microscope, comprising a system for generating at least a desired pattern of light, the system comprising:
  a laser unit adapted to emit at least one input laser pulse having a duration below or equal to 10 picoseconds,
  a first acousto-optical deflector adapted to deflect a laser pulse in a first direction to obtain a first deflected laser pulse, and
  a second acousto-optical deflector adapted to deflect the first deflected laser pulse in a second direction to obtain a second deflected laser pulse, the first direction and the second direction defining at least an angle comprised between 85° and 95°, and
  an optic system adapted to send the second deflected laser pulse, to obtain a desired pattern of light within the sample,
characterized in that:
  each acousto-optic deflector comprises an acousto-optical crystal and a transducer adapted to command the crystal by applying an acoustic wave, the laser unit and the acousto-optical deflectors being synchronized such that each acousto-optic deflector only interacts with a laser pulse when the spatial pattern of acoustic wave is established at the appropriate coordinates in the crystal optic window,
  the first acousto-optical deflector is further adapted to spatially shape the first deflected laser pulse in phase and in amplitude according to a first function,
  the second acousto-optical deflector is further adapted to spatially shape the second deflected laser pulse in phase and in amplitude according to a second function, and
  both the first function f and the second function g are such that a desired pattern of light is obtainable by holography through the optic system.

14. The non-linear microscope according to claim 13, wherein the laser unit comprises a femtosecond pulsed laser and a regenerative amplifier.

15. The non-linear microscope according to claim 13, wherein the non-linear microscope is a two-photon microscope.

* * * * *